US012776400B2

(12) United States Patent
Peng et al.

(10) Patent No.: US 12,776,400 B2
(45) Date of Patent: Oct. 27, 2026

(54) GENERATING CLINICAL DOCUMENTATION USING LARGE LANGUAGE MODELS AND ARTIFICIAL INTELLIGENCE

(71) Applicant: Orchid Exchange Inc., Wilmington, DE (US)

(72) Inventors: Yipeng Peng, Philadelphia, PA (US); Joseph Pomianowski, Philadelphia, PA (US); Soo Yeon Lee, Seoul (KR)

(73) Assignee: ORCHID EXCHANGE INC., Wilmington, DE (US)

( * ) Notice: Subject to any disclaimer, the term of this patent is extended or adjusted under 35 U.S.C. 154(b) by 0 days.

(21) Appl. No.: 18/967,365

(22) Filed: Dec. 3, 2024

(65) Prior Publication Data

US 2026/0066066 A1 Mar. 5, 2026

Related U.S. Application Data

(60) Provisional application No. 63/688,238, filed on Aug. 28, 2024.

(51) Int. Cl.

| | |
|---|---|
| ***G16H 10/60*** | (2018.01) |
| ***G06F 40/186*** | (2020.01) |

(Continued)

(52) U.S. Cl.

CPC ........... *G16H 10/60* (2018.01); *G06F 40/186* (2020.01); *G10L 15/183* (2013.01); *G16H 15/00* (2018.01); *G16H 50/20* (2018.01); *G16H 80/00* (2018.01)

(58) Field of Classification Search

None

See application file for complete search history.

(56) References Cited

U.S. PATENT DOCUMENTS

| | | | |
|---|---|---|---|
| 8,612,261 | B1 | 12/2013 | Swanson et al. |
| 8,738,396 | B2 | 5/2014 | Green, III et al. |

(Continued)

FOREIGN PATENT DOCUMENTS

| | | | | |
|---|---|---|---|---|
| DE | 102022211036 A1 | 4/2024 | | |
| WO | WO-2025111541 A1 * | 5/2025 | ......... | G06Q 10/0633 |
| WO | WO-2025147613 A1 * | 7/2025 | ........... | G06N 3/0475 |

OTHER PUBLICATIONS

Jixuan Wang, Jingbo Yang, Haochi Zhang, Helen Lu, Marta Skreta, Mia Husić, Aryan Arbabi, Nicole Sultanum & Michael Brudno; PhenoPad: Building AI enabled note-taking interfaces for patient encounters; Jan. 27, 2022; URL: https://www.nature.com/articles/s41746-021-00555-9 (Year: 2022).*

(Continued)

*Primary Examiner* — Richa Sonifrank
(74) *Attorney, Agent, or Firm* — Jonathan M. Waldman

(57) ABSTRACT

Systems and methods generate clinical documentation using large language models and artificial intelligence (AI). A template management module is provided to create customizable templates. A processing unit can receive input data from various sources and use AI to generate transcripts, summarize sessions, and produce clinical documentation such as clinical notes. The processing unit may also generate Current Procedural Terminology (CPT) and diagnosis codes, generate after-visit summaries, and generate referral letters. The AI may be trained on past clinical notes and can adapt to the clinician's style over time, with a feedback loop for continuous improvement. Additional features include cohort-based training, real-time language translation, predictive text, and analytics for documentation trends. The system supports customization of note length, style, and keywords, as well as integration with external medical databases and patient portals.

11 Claims, 6 Drawing Sheets

(51) Int. Cl.
*G10L 15/183* (2013.01)
*G16H 15/00* (2018.01)
*G16H 50/20* (2018.01)
*G16H 80/00* (2018.01)

(56) References Cited

U.S. PATENT DOCUMENTS

| | | | | |
|---|---|---|---|---|
| 10,692,594 | B2 | 6/2020 | Rhodes et al. | |
| 10,949,602 | B2 * | 3/2021 | Snider | G10L 15/26 |
| 11,049,594 | B2 | 6/2021 | Chintamaneni | |
| 11,152,121 | B2 | 10/2021 | Stoval, III et al. | |
| 11,227,688 | B2 | 1/2022 | Strader et al. | |
| 11,361,853 | B2 | 6/2022 | Stern | |
| 11,373,739 | B2 | 6/2022 | Ozeran | |
| 11,494,735 | B2 | 11/2022 | Drexel et al. | |
| 11,532,386 | B2 | 12/2022 | Petri et al. | |
| 11,961,197 | B1 * | 4/2024 | Morgan | G06T 19/006 |
| 12,261,933 | B2 * | 3/2025 | Salomon | G06F 21/602 |
| 12,361,228 | B2 * | 7/2025 | Sabapathy | G06F 16/345 |
| 2009/0177495 | A1 | 7/2009 | Abousy et al. | |
| 2011/0202370 | A1 * | 8/2011 | Green, III | G16H 10/60 705/3 |
| 2013/0311201 | A1 | 11/2013 | Chatfield et al. | |
| 2016/0154792 | A1 * | 6/2016 | Sarikaya | G06F 40/35 704/9 |
| 2017/0169379 | A1 * | 6/2017 | Horseman | G06Q 10/00 |
| 2017/0364640 | A1 | 12/2017 | Badawi | |
| 2019/0140995 | A1 * | 5/2019 | Roller | G06F 40/186 |
| 2019/0272900 | A1 | 9/2019 | Jancsary et al. | |
| 2021/0390249 | A1 | 12/2021 | Breber et al. | |
| 2022/0044812 | A1 | 2/2022 | Barnes et al. | |
| 2022/0147703 | A1 * | 5/2022 | Martinez | G06F 40/186 |
| 2022/0148689 | A1 * | 5/2022 | Gill | G16H 10/60 |
| 2023/0245651 | A1 * | 8/2023 | Wang | G06F 3/011 704/275 |
| 2023/0259698 | A1 * | 8/2023 | Kaku | G06F 40/279 704/235 |
| 2023/0368878 | A1 * | 11/2023 | Molenda | G16H 70/60 |
| 2024/0257931 | A1 * | 8/2024 | Ginsburg | G16H 20/10 |
| 2024/0304339 | A1 * | 9/2024 | Larusson | G16H 10/60 |
| 2024/0394089 | A1 * | 11/2024 | Kelly | G06F 9/45558 |
| 2024/0404669 | A1 * | 12/2024 | Shope | G16H 10/20 |
| 2024/0420846 | A1 * | 12/2024 | Hernandez | G16H 20/70 |
| 2025/0014731 | A1 * | 1/2025 | Soori-Arachi | G06Q 20/065 |
| 2025/0061291 | A1 * | 2/2025 | Gardner | G06F 16/345 |
| 2025/0118399 | A1 * | 4/2025 | Sasidharan | G16H 10/00 |
| 2025/0135287 | A1 * | 5/2025 | Bergmann-Good | G16H 20/70 |
| 2025/0166764 | A1 * | 5/2025 | Chang | G06V 10/77 |
| 2025/0166803 | A1 * | 5/2025 | Zhang | G16H 50/20 |
| 2025/0372213 | A1 * | 12/2025 | Shah | A61B 5/0011 |
| 2025/0384206 | A1 * | 12/2025 | Baird | G06F 40/186 |
| 2026/0148863 | A1 * | 5/2026 | Banaszak | G16H 50/70 |

OTHER PUBLICATIONS

Bongurala, Archana Reddy et al., "Transforming Health Care With Artificial Intelligence: Redefining Medical Documentation", Mayo Clinic Proceedings Digital Health 2(11), May 2024.

Veenendaal, Alexis, "Electronic Health Record (EHR) Automation", SS&C Blue Prism, Jan. 19, 2024, https://www.blueprism.com/resources/blog/electronic-health-record-ehr-automation/.

* cited by examiner

500

GENERATING CLINICAL DOCUMENTATION USING LARGE LANGUAGE MODELS AND ARTIFICIAL INTELLIGENCE

CROSS-REFERENCE TO RELATED APPLICATIONS

This application claims the benefit of priority to U.S. Provisional Patent Application No. 63/688,238, filed on Aug. 28, 2024, entitled "Generating Clinical Documentation Using Large Language Models and Artificial Intelligence," the contents of which are hereby incorporated by reference in its entirety.

BACKGROUND

Current clinical documentation processes are burdensome and time-consuming, involving manual transcription and summarization of patient data. Such methods are prone to errors, reducing productivity and detracting from patient care. Existing Electronic Health Record (EHR) systems often lack the flexibility and sophistication to handle a variety of clinical scenarios and emerging technologies like telehealth. These systems also generally do not provide advanced artificial intelligence (AI) capabilities for tailored documentation generation in alignment with clinician preferences.

Current clinical documentation methods involve significant manual effort, requiring healthcare professionals to transcribe and summarize patient data. This manual process is both time-consuming and prone to human error, detracting from the time available for direct patient care and potentially impacting the quality of documentation.

Existing EHR systems often fail to address the complexities and variability of clinical workflows. They generally lack advanced AI functionalities that could automate and enhance the accuracy of clinical documentation. Furthermore, these systems frequently do not integrate well with emerging healthcare technologies such as telehealth platforms, virtual reality (VR), and augmented reality (AR). This results in a fragmented data capture process, leading to inefficiencies in data management and interoperability challenges.

Moreover, the rigidity of current EHR systems hinders their ability to adapt to individual practitioner preferences and clinical specialties. Without a flexible and intelligent mechanism to tailor the documentation process, clinicians face difficulties in efficiently managing and retrieving patient information. This shortcoming not only affects the productivity of healthcare providers but also poses a risk to patient safety and care continuity due to potential inaccuracies in the medical records.

It is with respect to these and other considerations that the various aspects and embodiments of the present disclosure are presented.

SUMMARY

Systems and methods are provided that pertain to clinical documentation. Specifically, systems and methods are provided for automating the transcription, summarization, and structuring of clinical data by employing advanced artificial intelligence (AI) and natural language processing (NLP) techniques. Integration with existing healthcare IT systems, including Electronic Health Records (EHRs), is provided while adhering to privacy and security regulations.

In one aspect, a system for generating clinical documentation using AI is described, comprising a data acquisition module configured to receive clinical data from multiple sources such as dictation, telehealth sessions, and video files; a processing unit executing machine learning algorithms for transcription and summarization of received data; a template management module for applying customizable templates during the documentation process; and a clinician interface for displaying and reviewing the generated documentation.

One object of the technology is to streamline the clinical documentation process by leveraging AI to automate transcription and summarization, reducing the administrative burden on clinicians. Another object is to increase the accuracy and compliance of clinical documents with current and anticipated healthcare standards and regulations.

In an embodiment, the data acquisition module includes a real-time transcription feature capable of handling both audio and video data to ensure adaptability across various clinical environments. The processing unit may execute NLP techniques trained on clinical notes from multiple medical specialties, providing specialized interpretation.

In another aspect, a method for generating clinical documentation using AI is presented, involving the reception of clinical data from sources such as dictation, telehealth sessions, and uploaded media files; processing this data with AI algorithms for transcription and summarization; applying customizable templates for structured clinical documentation; and presenting the documentation for clinician review via a user interface that allows for real-time edits and feedback.

One object of the method is to enhance the flexibility of the clinical documentation process by allowing clinicians to apply customizable templates at any stage, ensuring that evolving clinical practices can be accommodated. Another object is to facilitate comprehensive clinical decision-making by integrating patient history data from EHRs into the AI-generated documentation.

In yet another embodiment, the processing unit is further configured to execute algorithms that dynamically update as new clinical guidelines and documentation practices develop. The system features a security module to ensure compliance with data protection regulations such as The Health Insurance Portability and Accountability Act of 1996 (HIPAA) and The General Data Protection Regulation (Regulation (EU) 2016/679) (GDPR).

In yet another aspect, another system for generating clinical documentation using AI is disclosed, featuring a data ingestion module for receiving data from sources including traditional formats and emerging virtual reality/augmented reality (VR/AR) platforms; a processing engine capable of adapting to advances in machine learning and NLP; and a template application module for clinician-defined templates that accommodate future documentation standards.

One object of this system is to integrate next-generation data sources and technologies with clinical documentation processes, ensuring adaptability to future healthcare information technology (IT) infrastructures. Another object is to provide robust security measures that safeguard clinical data against unauthorized access and comply with evolving privacy regulations.

In yet another embodiment, the described systems and methods incorporate AI-driven algorithms that are updated based on clinician feedback and adjustments in clinical guidelines, ensuring continuous improvement and accuracy in clinical documentation.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
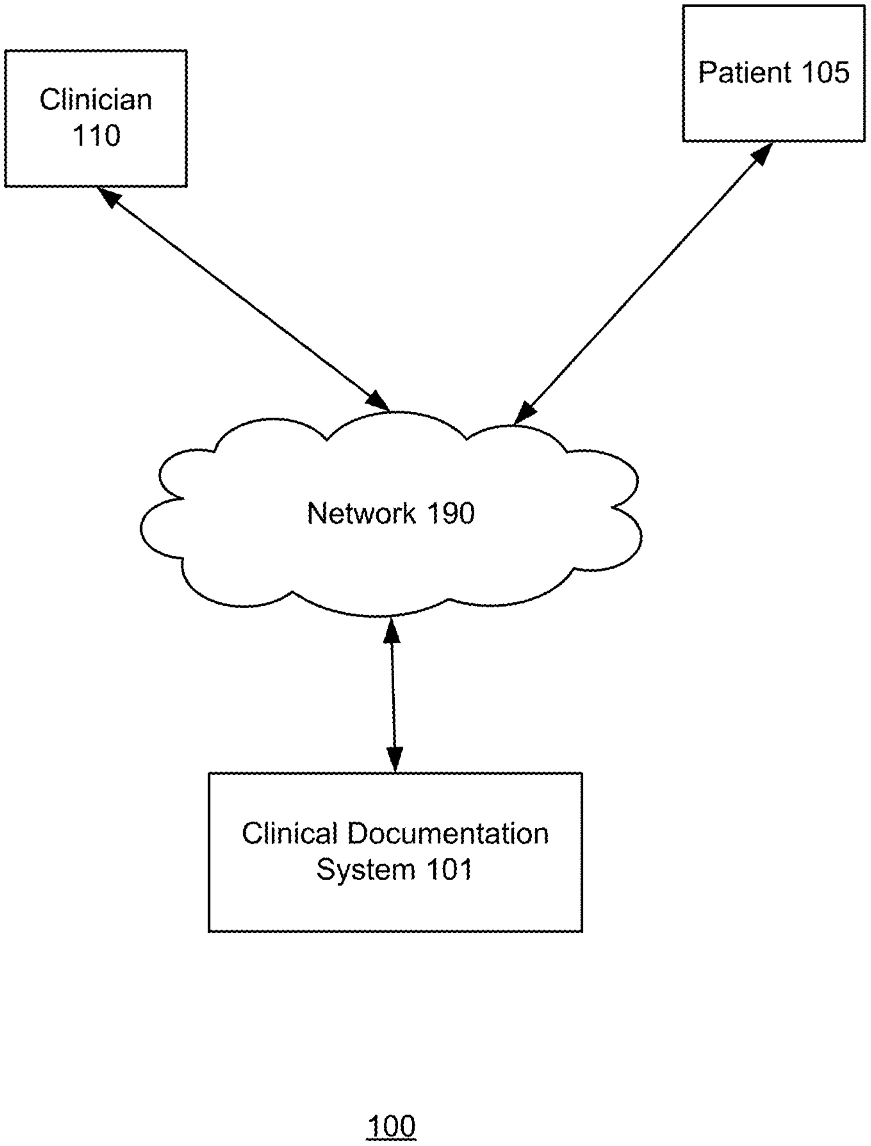
FIG. 1 is an example environment for generating clinical documentation using large language models and AI.

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

FIG. 1 is an example environment 100 for generating clinical documentation using large language models and AI. As shown, the environment 100 includes a patient 105, a clinician 110, and a clinical documentation system 101 communicating through a network 190. While only one clinician 110 and one patient 105 are shown, it is contemplated that there may be multiple clinicians 110 and/or patients 105 in the environment 100. The network 190 may be a variety of network types including, but not limited to, the public switched telephone network (PSTN), a cellular telephone network, and a packet switched network (e.g., the Internet). In some implementations, the clinician 110, the patient 105, and the clinical documentation system 101 may be in communication with one another variously through more than one network or network type.

The clinician 110 as used herein may include any provider of healthcare and medical services including mental health services. The clinician 110 may include solo practitioners as well as group practices that include multiple practitioners. Clinicians 110 may include healthcare providers, wellness providers, therapists, psychologists, psychiatrists, or some combination of all. Patients 105 may be any individual that receives medical or healthcare services from a clinician 110.

As described further herein, a clinical documentation system, such as the clinical documentation system 101, provides transcription, summarization, and structuring of clinical data by leveraging advanced artificial intelligence (AI) and natural language processing (NLP) techniques, ensuring integration with healthcare information technology (IT) systems like Electronic Health Records (EHRs), while adhering to privacy and security regulations. The clinical documentation system 101 overcomes conventional inefficiencies and inaccuracies and enables clinicians 110 to maintain accurate documentation with reduced manual effort, thereby improving the overall quality of patient 105 care and operational efficiency within healthcare environments.

As described further herein, the clinical documentation system 101 provides functionality to generate clinical documentation using large language models and AI. The clinical documentation system 101 provides functionality to create customizable templates. The clinical documentation system 101 also provides functionality to receive input data from various sources and use AI to generate transcripts, summarize sessions, and produce clinical documentation such as clinical notes, as well as generate Current Procedural Terminology (CPT) and diagnosis codes, generate after-visit summaries, and generate referral letters. The AI may be trained on past clinical notes and can adapt to the clinician's style over time, with a feedback loop for continuous improvement. Additional features include cohort-based training, real-time language translation, predictive text, and analytics for documentation trends. The clinical documentation system 101 supports customization of note length, style, and keywords, as well as integration with external medical databases and patient portals.

Figure 2:
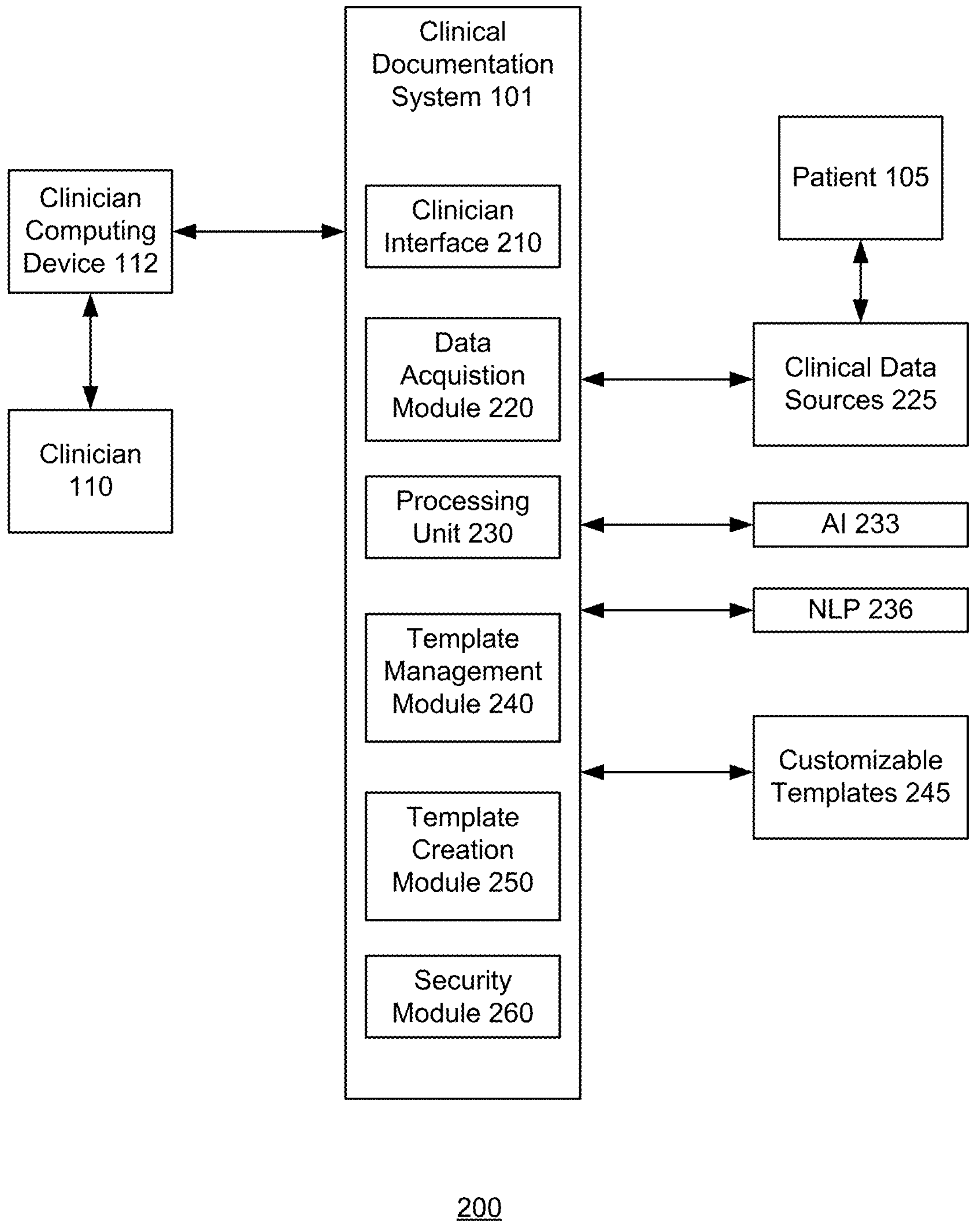
FIG. 2 is an illustration of an example clinical documentation system.

FIG. 2 is an illustration of an example clinical documentation system 101 in an environment 200. The clinical documentation system 101 comprises a clinician interface 210, a data acquisition module 220, a processing unit 230, a template management module 240, a template creation module 250, and security module 260. More or fewer components may be supported. Some or all of the components of the clinical documentation system 101 may be implemented together or separately by a general purpose computing device such as the computing device 600 illustrated with respect to FIG. 6. In addition, some or all of the components may be implemented together or separately by a cloud-based computing environment.

In some implementations, the clinician 110 may interact with the clinical documentation system 101 via a clinician computing device 112 in communication with the clinician interface 210. In other implementations, the clinician 110 may interact with the clinical documentation system 101 directly via the clinician interface 210 without the need for a clinician computing device 112.

Figure 6:
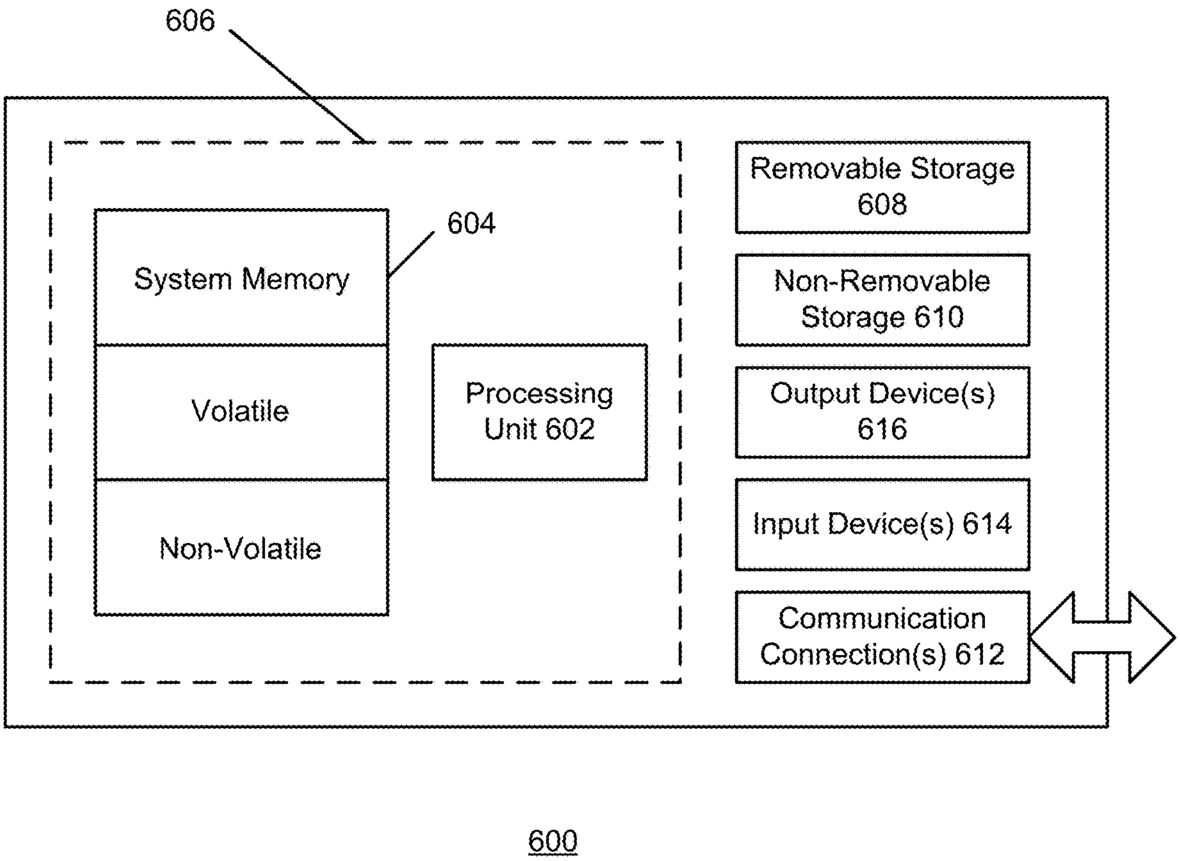
FIG. 6 shows an exemplary computing environment in which example embodiments and aspects may be implemented.

The clinical documentation system 101 and the clinician computing device 112 may each be implemented using a variety of computing devices such as smartphones, desktop computers, laptop computers, and tablets. Other types of computing devices may be supported. A suitable computing device is illustrated in FIG. 6 as the computing device 600. In some implementations, the clinical documentation system 101 and the clinician computing device 112 may be in communication with each other without a network connection.

The clinician interface 210 facilitates real-time interaction between the clinician 110 (via the clinician computing device 112) and the clinical documentation system 101. The clinician interface 210 allows the clinician 110 to review the AI-generated documentation, make edits, and provide structured feedback. This feedback loop provides continuous improvement of the clinical documentation system 101, as it enables the AI to learn and adapt to the clinician's style and preferences over time.

The data acquisition module 220 is configured to receive clinical data from multiple sources, shown as clinical data sources 225, including but not limited to dictation, telehealth session recordings, and uploaded audio or video files. The module 220 is adaptable to future data formats, ensuring long-term usability as new technologies emerge. This adaptability is crucial for maintaining the system's relevance in an ever-evolving healthcare landscape. Clinical data sources 225 receive and/or maintain data pertaining to the patient 105.

The processing unit 230 is the core engine of the clinical documentation system 101, responsible for executing AI-driven algorithms that transcribe and summarize the acquired clinical data. The processing unit 230 may use AI 233 and NLP 236 in its processing of the data and its generation of clinical documentation.

The processing unit 230 is equipped with machine learning capabilities that allow it to adapt to various data formats and contextual variations. For example, the processing unit 230 can process audio data from dictation differently than video data from a telehealth session, ensuring that the output is accurate and contextually appropriate.

Additionally, the processing unit 230 integrates NLP techniques, trained on clinical notes across multiple medical specialties, including behavioral health. This specialized training enables the clinical documentation system 101 to provide interpretations tailored to specific clinical contexts, enhancing the accuracy and relevance of the generated documentation.

The template management module 240 allows the clinician 110 to select and apply customizable templates 245 at any point in the clinical documentation process, whether before, during, or after the data acquisition and processing stages. This flexibility ensures that the structured clinical documentation can be tailored to the specific needs of each clinical encounter as it progresses. Customizable templates may be created using the template creation module 250.

The clinician 110 can choose templates from a predefined library or create their own, offering extensive adaptability to meet the diverse requirements of various clinical practices. The design of the template management module 240 ensures that the selected templates comply with both current and anticipated documentation standards, to help maintain regulatory alignment.

A security module 260 provides security to the data maintained by, and documentation created by, the clinical documentation system 101. Given the sensitive nature of clinical data, the security module 260 is configured to ensure compliance with privacy and security regulations. The security module 260 is configured to adapt to existing and future data protection regulations, including updates to state privacy laws, HIPAA, GDPR, and other relevant international standards. The security module 260 ensures that all clinical data is processed and stored securely, protecting patient confidentiality and maintaining the integrity of the clinical documentation system 101.

Figure 3:
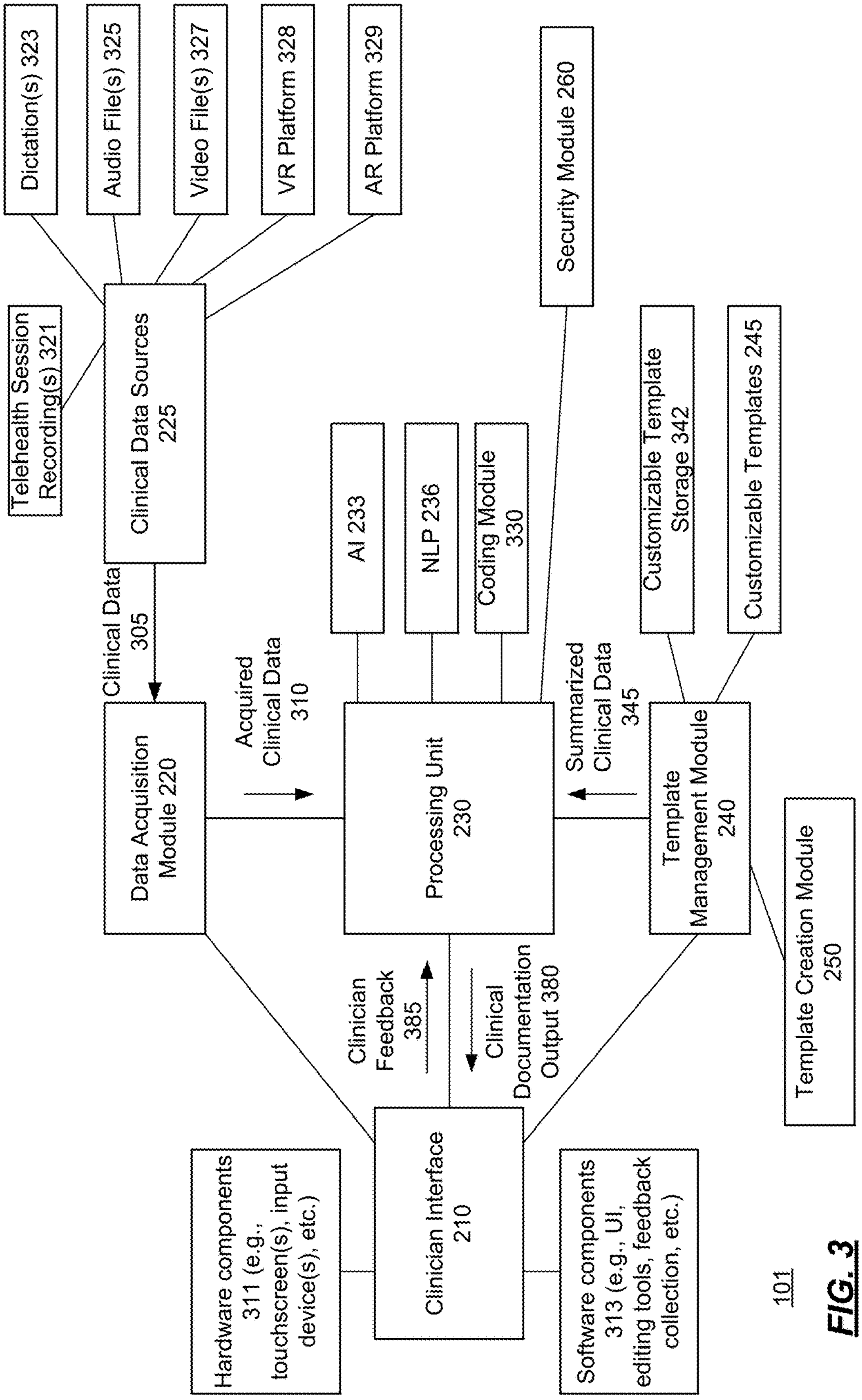
FIG. 3 is another illustration of an example clinical documentation system.

FIG. 3 illustrates additional details of an example clinical documentation system 101. As described further herein, in operation, the clinical documentation system 101 receives clinical data from various clinical data sources 225 through the data acquisition module 220. The processing unit 230 transcribes and summarizes the data using AI-driven algorithms, tailoring the output to the specific clinical context. Using the clinician computing device 112 or directly via the clinician interface 210, the clinician 110 can select or create a template through the template management module 240, which is then applied to the summarized data to generate structured clinical documentation 380. The clinician interface 210 allows for real-time review and modification of the documentation 380, with any changes or feedback 385 provided being used to refine future documentation processes. The security module 260 ensures that all data handling complies with applicable privacy and security standards, safeguarding patient information throughout the process.

The clinician interface 210 may include hardware components 311 such as one or more touchscreen displays (e.g., high-resolution displays for interaction) and inputs devices such as keyboards, mice, and microphones for voice commands.

The clinician interface 210 may include software components 313 such as a user interface (UI) for straightforward navigation and interaction, and real-time editing tools that enable the clinician 110 to make real-time edits. An integrated feedback 385 collection system may be provided for structured clinician feedback.

In some implementations, the clinician interface 210 is an interactive component that presents the AI-generated documentation for clinician review and real-time edits. It also collects feedback 385 to refine AI algorithms, forming a continuous improvement loop. It is contemplated that the UI can include voice-controlled or gesture-based controls, along with automated suggestions for document verification.

Depending on the implementation, the data acquisition module 220 may comprise hardware components such as microphones (e.g., high-sensitivity MEMS microphones) and cameras (e.g., 4K resolution cameras) for capturing high-quality audio and video data. The data acquisition module 220 may include sensors such as integrated sensors in VR/AR platforms for capturing motion tracking and physiological data. Additionally, the data acquisition module 220 may include connectivity interfaces such as multiple ports and wireless receivers to connect with external medical devices, as well as storage buffers to act as temporary storage facilities for the incoming data before processing.

The data acquisition module 220 may comprise software components such as data capture APIs (e.g., interfaces to capture data from EHR systems, telehealth platforms, and file uploads). The data acquisition module 220 may also include format conversion tools to convert data into system-compatible formats (e.g., WAV for audio, MP4 for video). Data validation scripts may be used to ensure the integrity and quality of captured data.

In operation, the data acquisition module 220 captures clinical data 305 from clinical data sources 225 such as telehealth session recordings 321, clinician dictations 323, audio files 325, video files 327, VR platforms 328, and AR platforms 329. The data acquisition module 220 ensures data formats are compatible or converts them as needed, validating the data for subsequent processing.

The data acquisition module 220 can be adapted to accept alternative data input methods including pre-recorded files and direct electronic medical record (EMR) inputs, utilizing different preprocessing techniques like noise reduction and signal enhancement.

In some implementations, the processing unit 230 may include hardware components such as high-performance processors (e.g., CPUs, GPUs, and specialized AI accelerators (TPUs, FPGAs)), as well as memory units (e.g., highcapacity RAM and high-bandwidth memory). Data buses such as high-speed connections may be used for efficient data transfer.

The processing unit 230 may include software components such as AI algorithms 233 and NLP models 236, implemented using frameworks like TensorFlow or PyTorch for transcription and NLP tasks, and pre-trained and fine-tuned models for medical terminology. Video and audio analysis tools may also be implemented with processing unit 230 comprising algorithms capable of extracting relevant clinical information from video and audio data. A coding module 330 may be provided and configured to automatically generate Current Procedural Terminology (CPT) and International Classification of Diseases (ICD) codes based on the content and structure of the AI-generated clinical documentation, ensuring alignment with healthcare regulatory standards.

In operation, the processing unit 230 converts audio data into text using AI-driven transcription algorithms, and employs NLP techniques to summarize the transcribed text, ensuring accurate contextual adaptation for different medical specialties. Video data is analyzed to extract visual cues relevant to clinical documentation. It is contemplated that alternative operations can be introduced, such as different machine learning models for enhanced accuracy or switching the order of video analysis and NLP processing.

The template management module 240 may include software components such as a template library which comprises a database containing predefined templates for various clinical encounters, a template editor which may act as an interface for clinicians to create and modify templates, and a template application engine which may be configured to apply selected templates to processed data.

In operation, the template management module 240 allows the selection and application of predefined templates and/or customizable templates 245 to summarize clinical data, enabling real-time modifications. It organizes the processed data into structured documentation aligning with specific clinical needs and provides summarized clinical data to the processing unit. Customizable templates may be generated by the template creation module 20 and stored in a customizable template storage 342. It is contemplated that in some implementations, automated template selection may be performed based on data type or context and that dynamic template application may be implemented as data is being processed.

The security module 260 ensures all clinical data is securely encrypted during transmission and storage. It continuously monitors compliance with privacy regulations and maintains audit logs.

The security module 260 may include hardware components such as secure servers (e.g., servers with hardware-level encryption), and firewalls and intrusion detection systems (IDSs) that monitor and log network activity for potential security breaches.

The security module 260 may include software components such as encryption algorithms (e.g., advanced encryption standards such as AES-256), compliance management tools that enforce HIPAA, GDPR, and other regulations, and audit logging that records access and modifications. It is contemplated that the security module 260 can include implementations of advanced encryption, such as post-quantum cryptography, and the use of solid state drives (SSDs) with built-in encryption.

Figure 4:
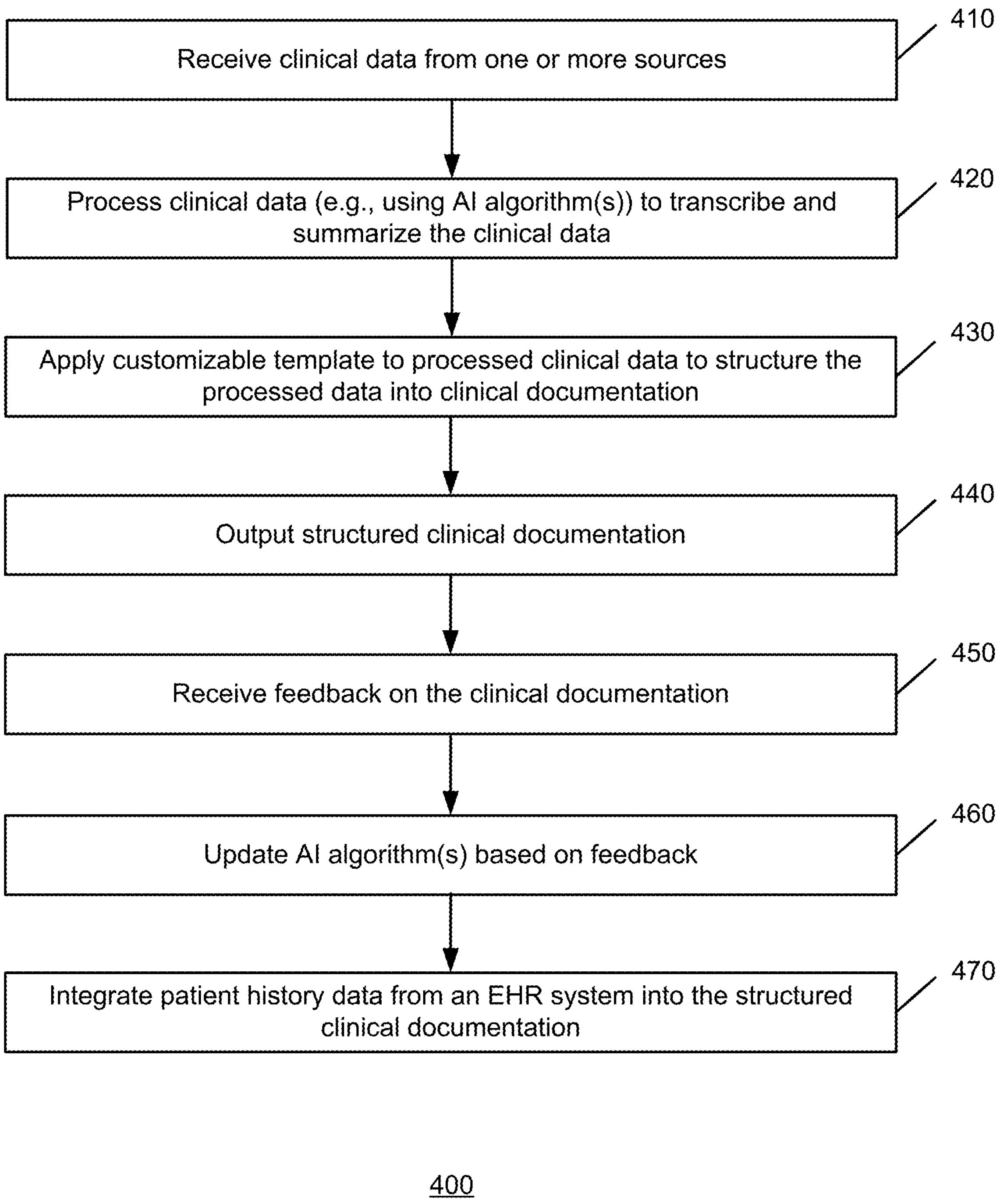
FIG. 4 is an operational flow of an implementation of a method for generating clinical documentation.

FIG. 4 is an operational flow of an implementation of a method 400 for generating clinical documentation. The method 400 may be implemented by a clinical documentation system such as the clinical documentation system 101, for example.

At 410, clinical data is received from one or more sources, such as the clinical data sources 225. The clinical data sources may include dictation (e.g., clinician voice recordings are captured, which may include patient consultations, diagnostic notes, or treatment plans), telehealth sessions (e.g., audio and video data from remote consultations or virtual appointments), uploaded files (e.g., pre-existing audio and/or video files that contain relevant clinical information), and emerging technologies such as VR and/or AR platforms.

At 420, the clinical data is processed to transcribe and summarize the clinical data. AI is used in the processing of the clinical data. The clinical data may be processed using one or more AI algorithms. Transcription, textual analysis, and summarization may be performed.

In transcribing the data, the system processes the acquired data using AI-driven algorithms to convert spoken language and audio data into text. Clinician dictations may convert telehealth session audio into text (e.g., speech to text conversion). Video analysis may be performed to extract relevant information from video data (e.g., identifying non-verbal cues during telehealth sessions).

In summarizing the data, the system may use NLP to analyze the transcribed text and create a concise summary. The system adapts to various medical specialties, ensuring that the summary accurately reflects the clinical context (e.g., behavioral health, speech pathology, physical therapy, general surgery, etc.). Additionally, the system is configured to adapt to different data formats and contextual variations.

At 430, the processed data is structured into clinical documentation by applying a customizable template to the processed data.

The system allows clinicians to select and apply a customizable template at any point in the process—before, during, or after data acquisition and processing. Selection may be from a library of pre-defined templates (e.g., SOAP (subjective, objective, assessment, and plan) notes for general practice, DAP (data, assessment, and plan) notes for a therapeutic session) based on the type of clinical encounter. Clinicians can create or modify templates to meet specific documentation needs. Structured documentation can be generated at multiple points depending on when the template is selected. Additionally, the system formats the documentation according to predefined standards and clinician preferences.

At 440, the clinical documentation is outputted. The clinical documentation may be outputted to a clinician computing device such as the clinician computing device 112 and/or a clinician interface such as the clinician interface 210, for real-time clinician edits and other feedback.

In an implementation, the structured clinical documentation is presented to the clinician via a user interface. Clinicians can view and edit the documentation in real-time. The clinician provides feedback on the AI-generated documentation. The system uses the feedback to refine future documentation, improving the AI's performance over time.

At 450, feedback is received on the clinical documentation. The feedback may be provided by the clinician via the clinician computing device and/or the clinician interface.

At 460, the AI algorithm(s) are updated using the feedback. The system continuously updates its AI algorithms based on clinician feedback and changes in clinical guidelines. The AI adapts to new data, improving accuracy and relevance in future documentation.

In some implementations, after review and any necessary edits, the clinician finalizes the clinical documentation. The system may confirm that the documentation meets all required standards and preferences. The system may generate additional documents based on the clinical notes. Such additional documents include coding (e.g., CPT and ICD codes) for billing and diagnosis purposes, and after-visit summary documents (e.g., for patient review), and referral letters which can be customized by the clinician. The finalized documentation is stored securely and integrated with other healthcare IT systems.

At 470, the patient history from an EHR system may be integrated into the clinical documentation. Thus, the documentation is added to the patient's EHR with the data being stored in compliance with privacy regulations (e.g., HIPAA, GDPR).

Figure 5:
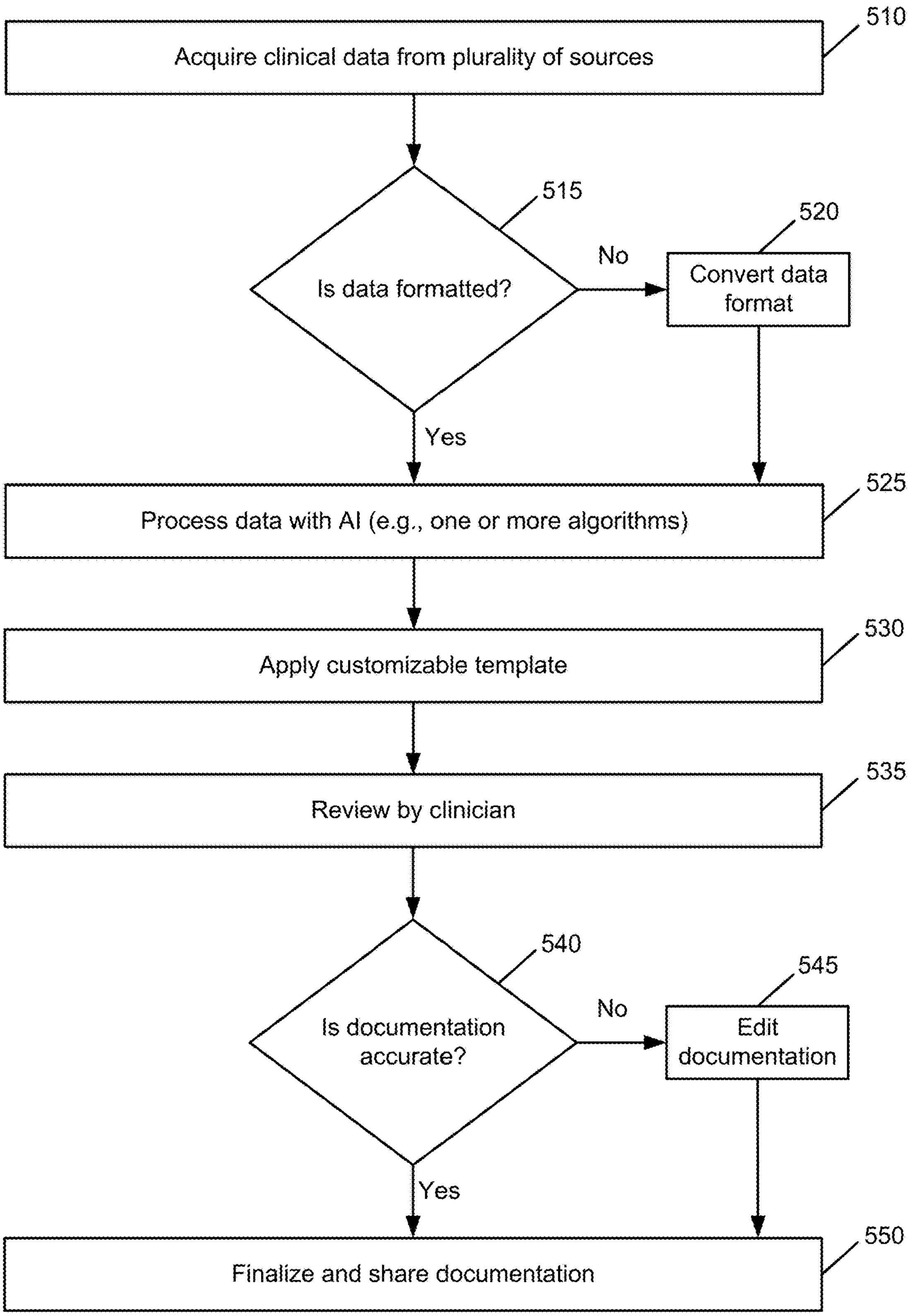
FIG. 5 is an operational flow of another implementation of a method for generating clinical documentation.

FIG. 5 is an operational flow of another implementation of a method 500 for generating clinical documentation. The method 500 comprises acquiring clinical data from multiple sources, processing the data using AI algorithms, applying a customizable template, presenting structured data via a user interface, determining if further editing is required, and if so, reviewing and editing notes, accepting structured feedback, and finalizing the clinical documentation. The method 500 may be implemented by a clinical documentation system such as the clinical documentation system 101, for example.

At 510, clinical data is acquired from a plurality of sources, such as the clinical data sources 225 (e.g., dictation, telehealth session recordings, uploaded audio and/or video files, etc.). In some implementations, clinical data may be acquired from a single source.

At 515, it is determined whether the data is formatted. If the data is formatted, then processing continues at 525. If the data is not formatted, then the data format is converted at 520, and processing continues at 525.

At 525, the data is processed with AI, such as by using one or more AI algorithms. The collected data undergoes processing by AI algorithms. These algorithms perform tasks like transcription of audio data and summarization of the clinical information, ensuring that data is effectively analyzed for subsequent steps.

At 530, a customizable template is applied to the processed data. This involves applying a selected customizable template to the processed data. This operation structures the data into a format suitable for clinical documentation, tailored to the specific needs of the clinician and the encounter type.

At 535, a clinician may review the output from the customizable template. Here, the structured data is presented to the clinician through a user interface. This interface allows real-time interaction and enables the clinician to review the documentation generated by the AI.

At 540, it is determined whether the documentation is accurate. If so, the documentation is finalized and shared at 550. If the documentation is determined to be inaccurate, then the documentation may be edited at 545, and then finalized and shared at 550.

At 545, if further editing is needed, the clinician can make necessary modifications to ensure the accuracy and completeness of the documentation. Once the notes are reviewed and edited, structured feedback from the clinician is accepted and integrated, forming a basis for refining and improving the AI algorithms for future documentation processes.

At 550, the clinical documentation is finalized based on the edits and feedback. This operation ensures that the documentation is complete, accurate, and ready for inclusion in the patient's EHR and/or other medical records systems.

Thus, the systems and methods described herein provide advanced AI and NLP integration with enhanced accuracy and context-specific documentation. Customizable templates allow for real-time modifications to meet diverse clinical needs. Clinician feedback ensures ongoing accuracy and efficiency. Multimodal data processing provides comprehensive processing capabilities for diverse data sources. Robust security measures provide advanced privacy protection and compliance adherence. Real-time interaction facilitates immediate documentation adjustments.

The systems and methods described herein are designed to be highly adaptable, with various embodiments and implementations possible depending on the specific clinical setting or technological advancements. For example, the data acquisition module can be configured to integrate with VR or AR platforms, capturing data from immersive telehealth sessions. The processing unit can be updated to incorporate the latest advancements in AI and machine learning, ensuring that the system remains at the forefront of clinical documentation technology.

Alternative embodiments may also include different configurations of the clinician interface, such as voice-command capabilities or integration with wearable devices. These alternatives provide flexibility in how the system is implemented, allowing it to meet the diverse needs of clinicians across different specialties.

It is contemplated that modular components may be used, thereby allowing independent replacements or upgrades. Integration with other healthcare IT systems for comprehensive solutions is contemplated. The output formats and timings may be adjusted based on the implementation, along with continuous learning and dynamic updates for AI enhancement.

By streamlining the clinical documentation process through advanced AI and NLP techniques, the described systems and techniques effectively reduce administrative burdens while ensuring accurate and compliant clinical records, all adaptable to evolving technological and regulatory landscapes.

FIG. 6 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 6, an exemplary system for implementing aspects described herein includes a computing device, such as computing device 600. In its most basic configuration, computing device 600 typically includes at least one processing unit 602 and memory 604. Depending on the exact configuration and type of computing device, memory 604 may be volatile (such as random access memory (RAM)), non-volatile (such as read-only memory (ROM), flash memory, etc.), or some combination of the two. This most basic configuration is illustrated in FIG. 6 by dashed line 606.

Computing device 600 may have additional features/functionality. For example, computing device 600 may include additional storage (removable and/or non-removable) including, but not limited to, magnetic or optical disks or tape. Such additional storage is illustrated in FIG. 6 by removable storage 608 and non-removable storage 610.

Computing device 600 typically includes a variety of computer readable media. Computer readable media can be any available media that can be accessed by the device 600 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 604, removable storage 608, and non-removable storage 610 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media may be part of computing device 600.

Computing device 600 may contain communication connection(s) 612 that allow the device to communicate with other devices. Computing device 600 may also have input device(s) 614 such as a keyboard, mouse, pen, voice input device, touch input device, etc. Output device(s) 616 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

As used herein, the singular form “a,” “an,” and “the” include plural references unless the context clearly dictates otherwise. As used herein, the terms “can,” “may,” “optionally,” “can optionally,” and “may optionally” are used interchangeably and are meant to include cases in which the condition occurs as well as cases in which the condition does not occur.

Ranges can be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as “about” that particular value in addition to the value itself. For example, if the value “10” is disclosed, then “about 10” is also disclosed.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for generating clinical documentation using large language models or artificial intelligence (AI), comprising:

a data acquisition module configured to receive clinical data from a clinician-supplied data stream, wherein the clinician-supplied data stream comprises at least one of dictation, telehealth session audio recordings, telehealth session video recordings, uploaded audio files, and uploaded video files;

a template creation module configured to allow a clinician to create a customizable template to meet requirements of a clinical practice of the clinician, wherein the customizable template is adaptable to meet diverse requirements of a plurality of different clinical practices;

a template management module configured to allow a selection of the customizable template and ensure that the customizable template complies with documentation standards and to maintain regulatory alignment, the template management module comprising a template editor configured to act as an interface for the clinician to modify the customizable template and permit real-time modifications to the customizable template;

a processing unit configured to execute a machine learning algorithm to:
(i) generate a transcription of the clinical data;
(ii) receive the clinician-supplied data stream;
(iii) generate an AI-generated summary of at least a portion of the clinical data in accordance with configuration data;
(iv) generate, using a large language model engine, a draft clinical note using at least one of the transcription, an automatically generated summarization of the transcription, and a user-inputted summarization; and
(v) apply the customizable template to the draft clinical note to structure data from the draft clinical note into structured clinical documentation;

the template management module further configured to:
enable a selection of the customizable template, at any stage of a clinical documentation workflow comprising the stages (i)-(v) and including before, during, and after any of the stages (i)-(v), wherein the selection is based on data type or clinical context, and
responsive to the selection and dynamically as data is being processed, apply the customizable template, at any stage of the clinical documentation workflow, to any of the transcription, the AI-generated summary, a clinician-provided synopsis, and the draft clinical note;

a coding module configured to automatically generate medical codes using a content and a structure of the structured clinical documentation; the coding module is further configured to comply with healthcare regulatory standards; and a clinician interface configured to:
display the draft clinical note and the structured clinical documentation, and
capture feedback for iterative refinement of subsequent clinical documentation.

2. The system of claim 1, wherein the data acquisition module comprises a real-time transcription feature configured to transcribe both audio data and video data and to provide adaptability across a plurality of clinical environments.

3. The system of claim 1, wherein the data acquisition module is adaptable to a plurality of data formats.

4. The system of claim 1, wherein the processing unit is further configured to execute natural language processing (NLP) techniques trained on clinical notes across a plurality of medical specialties to provide specialized interpretation.

5. The system of claim 4, wherein the plurality of medical specialties includes behavioral health.

6. The system of claim 1, wherein the medical codes comprise Current Procedural Terminology (CPT) and International Classification of Diseases (ICD) codes.

7. The system of claim 1, wherein the at least one structured clinical documentation comprises at least one of a Current Procedural Terminology (CPT) code or an International Classification of Diseases (ICD) code.

8. The system of claim 1, wherein the structured clinical documentation comprises a treatment plan derived from the draft clinical note.

9. The system of claim 1, wherein the template management module is configured to apply the customizable template to the draft clinical note before the structured clinical documentation is generated.

10. The system of claim 1, wherein the clinician interface is configured to capture feedback in a structured format that is used to retrain at least one machine learning model in the processing unit.

11. The system of claim 1, wherein the data acquisition module is further configured to receive at least one of physiological-sensor data, data originating from a virtual-reality platform, and data originating from an augmented-reality platform.

* * * * *